United States Patent [19]
Ladner et al.

[11] Patent Number: 5,770,412
[45] Date of Patent: Jun. 23, 1998

[54] AZIDO-CAPROLACTAM AS INHIBITOR FOR SELECTING MICROORGANISMS WITH HIGH LYSINE PRODUCTIVITY

[75] Inventors: Wolfgang Ladner, Fussgoenheim; Uwe Pressler, Altrip; Wolfgang Siegel, Mannheim, all of Germany

[73] Assignee: BASF Aktiengesellschaft, Ludwigshafen, Germany

[21] Appl. No.: 614,264

[22] Filed: Mar. 12, 1996

Related U.S. Application Data

[63] Continuation of Ser. No. 280,586, Jul. 25, 1994, abandoned, which is a continuation-in-part of Ser. No. 181,973, Jan. 18, 1994, abandoned, which is a continuation of Ser. No. 927,680, Sep. 3, 1992, abandoned.

[30] Foreign Application Priority Data

Jul. 25, 1990 [DE] Germany .......................... 40 23 576.9

[51] Int. Cl.[6] .............................. C12N 15/00; C12P 13/08
[52] U.S. Cl. .................... 435/172.1; 435/115; 435/252.1
[58] Field of Search ................................ 435/115, 172.1, 435/170, 34, 172.2, 252.1

[56] References Cited

U.S. PATENT DOCUMENTS

| | | | |
|---|---|---|---|
| 3,687,810 | 8/1972 | Kurihara et al. | 435/115 |
| 3,708,395 | 1/1973 | Nakayama et al. | |
| 4,066,501 | 1/1978 | Tosaka et al. | 435/115 |
| 4,411,997 | 10/1983 | Shimazaki et al. | 435/172.1 |

FOREIGN PATENT DOCUMENTS

| | | |
|---|---|---|
| 175309 | 9/1985 | European Pat. Off. . |
| 51-19186 | 2/1976 | Japan . |

OTHER PUBLICATIONS

ATCC Catalogue o Bacteria, 1989, pp. 46 and 66.
*Trends in Biotechnology*, vol. 1, 1983, Tosaka, "The Production of L–Lysine by Fermentation", pp. 70–74.
*Chemical Abstract*, vol. 85, 1976, p. 469, Nr. 92,192.

*Primary Examiner*—Irene Marx
*Attorney, Agent, or Firm*—Keil & Weinkauf

[57] ABSTRACT

A process for producing microorganisms which have increased L-lysine productivity is described. The process makes use of microorganisms of the genera Corynebacterium and Brevibacterium which are resistant to feedback inhibition by 2-azido-$\epsilon$-caprolactam.

3 Claims, No Drawings

AZIDO-CAPROLACTAM AS INHIBITOR FOR SELECTING MICROORGANISMS WITH HIGH LYSINE PRODUCTIVITY

This application is a continuation of application Ser. No. 08/280,586, filed Jun. 25, 1994, which is a c-i-p of Ser. No. 08/181,973, filed Jan. 18, 1994, which is a continuation of Ser. No. 07/927,680, which was filed Sep. 3, 1992 all now abandoned.

The present invention relates to a process for producing L-lysine and microorganisms therefor.

L-lysine is an essential amino acid and is widely used as additive to human and animal food. It is also employed in medicine as component of infusion solutions.

L-lysine is obtained by hydrolysis of proteins with acid, by synthesis of D,L-lysine and subsequent resolution of the racemate and by synthesis with the aid of microorganisms. Microbiological processes for preparing L-lysine are described, for example, in Trends in Biotechnology 1 (1983) 70–74.

We have found an improved process for producing microorganisms which produce L-lysine.

The present invention relates to a process for producing microorganisms which have increased L-lysine productivity by mutation of microorganisms of the genera Corynebacterium and Brevibacterium with known mutagens in a conventional manner, which comprises mutating strains of the abovementioned genera and selecting those resistant to feedback inhibition by 2-azido-ε-caprolactam.

Surprisingly, 2-azido-ε-caprolactam has considerably higher efficiency in the selection of mutants after mutagenesis than the compounds described in JP 51-19 186 and EP 175 309, such as fluoro- or chlorocaprolactam.

It is thus possible by selection with azidocaprolactam to increase the lysine productivity of strains by more than 10%.

The mutants according to the invention can be produced by conventional mutagenesis, eg. with N-methyl-N'-nitro-N-nitrosoguanidine or by U.V. radiation.

Examples of suitable microorganisms of the genera Corynebacterium (C) and Brevibacterium (B) are the following: *B. ammoniagenis, B. divaricatum, B. flavum, B. ketoglutamicum, B. lactofermentum, B. linens, B. sp., C. acetoacidophilum, C. acetoglutamicum, C. glutamicum, C. lilium* and *C. sp.* Preference is given to *B. flavum* and *C. glutamicum*, especially *B. flavum* ATCC 21.474 and *C. glutamicum;* ATCC 21526. The latter has the special advantage that it is homoserine-dependent and, moreover, is resistant to S-(2-aminoethyl)-L-cysteine.

As already indicated, it is beneficial for the strains to be homoserine-dependent. It is also useful for the strains to be resistant to S-(2-aminoethyl)-L-cysteine. If the strains do not possess this resistance it can be introduced as described in U.S. Pat. No. 3,707,441 by treating the strains with N-methyl-N'-nitro-N-nitrosoguanidine and subsequent selection.

EXAMPLE

*Corynebacterium glutamicum* ATCC 21 526 was treated with 250 μg/ml N-methyl-N'-nitro-N-nitrosoguanidine in tris/maleic acid buffer, pH 6.0, at 30° C. for 30 min. The cells were then washed with 0.1M tris buffer, pH 7.2, plated on minimal agar plates and then incubated at 28° C. for from 4 to 14 days.

The minimal agar had the following composition:

| | |
|---|---|
| 20 g/l agar | 0.1 g/l MnSO$_4$.H$_2$O |
| 2 g/l (NH$_4$)$_2$SO$_4$ | 100 μg/l biotin |
| 0.5 g/l KH$_2$PO$_4$ | 30 mg/l each Met, Thr, Leu |
| 0.5 g/l K$_2$HPO$_4$ | 4 g/l lactate |
| 0.4 g/l MgSO$_4$.7H$_2$O | 40 moles/l 2-azido-ε-caprolactam |
| 0.01 g/l FeSO$_4$.7H$_2$O | pH = 7.0 |

The colonies producing lysine amongst those growing on the agar plates after incubation were identified. The strains which produced 10% more lysine than the initial strain were isolated.

We claim::

1. A process for stably increasing L-lysine in L-lysine-producing bacteria by mutation and selection steps which process comprises
   a) mutating bacteria selected from the group consisting of *Brevibacterium ammoniagenes, Brevibacterium divaricatum, Brevibacterium flavum, Brevibacterium ketoglutamicum, Brevibacterium linens, Corynebacterium acetoacidophilum, Corynebacterium acetoglutamicum, Corynebacterium glutamicum,* and *Corynebacterium lilium* with one or more mutagens, and
   b) selecting strains that produce increased yields of L-lysine by culturing strains that survive said mutation step in a minimal medium having a concentration of 40 mM 2-azido-ε-caprolactam to select for mutants resistant to said compound, wherein said resistant strains produce increased yields of L-lysine.

2. The process of claim 1, wherein the bacteria to be mutated are selected from the group consisting of *Brevibacterium flavum* and *Corynebacterium glutamicum*.

3. The process of claim 2, wherein the bacteria to be mutated are selected from the group consisting of *B. flavum* ATCC 21,474 and *Corynebacterium glutamicum* ATCC 21,526.

* * * * *

UNITED STATES PATENT AND TRADEMARK OFFICE
CERTIFICATE OF CORRECTION

PATENT NO.: 5,770,412

DATED: June 23, 1998

INVENTOR(S): LADNER et al.

It is certified that error appears in the above-identified patent and that said Letters Patent is hereby corrected as shown below:

On the cover page, in item [63], "which is a continuation of Ser. No. 927,680, Sep. 3, 1992, abandoned." should read --which is a continuation of Ser. No. 927,680, abandoned, filed as PCT/EP 91/01316, July 13, 1991.--

Signed and Sealed this

Sixteenth Day of February, 1999

Attest:

*Acting Commissioner of Patents and Trademarks*

*Attesting Officer*